United States Patent
Soffiatti et al.

(10) Patent No.: US 9,750,538 B2
(45) Date of Patent: Sep. 5, 2017

(54) EXTERNAL FIXING DEVICE, FOR TREATING BONE FRACTURES

(71) Applicant: TECRES S.p.A., Sommacampagna (IT)

(72) Inventors: Renzo Soffiatti, Nogara (IT); Giovanni Faccioli, Monzambano (IT); Bruno Magnan, Verona (IT)

(73) Assignee: TECRES S.P.A., Sommacampagna (VR) (IT)

( * ) Notice: Subject to any disclaimer, the term of this patent is extended or adjusted under 35 U.S.C. 154(b) by 20 days.

(21) Appl. No.: 14/761,223

(22) PCT Filed: Jan. 21, 2014

(86) PCT No.: PCT/IB2014/058443
§ 371 (c)(1),
(2) Date: Jul. 15, 2015

(87) PCT Pub. No.: WO2014/111907
PCT Pub. Date: Jul. 24, 2014

(65) Prior Publication Data
US 2016/0022315 A1    Jan. 28, 2016

(30) Foreign Application Priority Data
Jan. 21, 2013  (IT) .............................. VR2013A0013

(51) Int. Cl.
*A61B 17/00* (2006.01)
*A61F 4/00* (2006.01)
(Continued)

(52) U.S. Cl.
CPC .............. *A61B 17/66* (2013.01); *A61B 17/60* (2013.01); *A61B 17/6416* (2013.01);
(Continued)

(58) Field of Classification Search
CPC ........................................... A61B 17/58–17/66
(Continued)

(56) References Cited

U.S. PATENT DOCUMENTS

| 2,238,870 A | * | 4/1941 | Haynes | ............... | A61B 17/6441 |
| | | | | | 403/56 |
| 2,346,346 A | * | 4/1944 | Anderson | .......... | A61B 17/6441 |
| | | | | | 403/76 |

(Continued)

FOREIGN PATENT DOCUMENTS

| EP | 0628289 A1 | 12/1994 |
| WO | WO95/10240 A1 | 4/1995 |

*Primary Examiner* — Eduardo C Robert
*Assistant Examiner* — Michelle C Eckman
(74) *Attorney, Agent, or Firm* — Tutunjian & Bitetto, P.C.

(57) ABSTRACT

An external fixing device for the treatment of bone fractures includes a first member, a second member, a central body arranged between the first member and the second member, a first ball joint for the articulated connection of the first member with the central body, a second ball joint for the articulated connection of the second member with the central body, locking means operatively associated to the first ball joint and with the second ball joint, respectively, the locking means being suitable for allowing/preventing the articulation of the first member and second member with respect to the central body, wherein the first member includes a first clamp, the second member includes a second clamp and the central body includes a third clamp for connection of the external fixing device to respective fractured bone portions to be treated.

23 Claims, 7 Drawing Sheets

(51) Int. Cl.
*A61F 5/04* (2006.01)
*A61B 17/66* (2006.01)
*A61B 17/64* (2006.01)
*A61B 17/60* (2006.01)

(52) U.S. Cl.
CPC ...... *A61B 17/6425* (2013.01); *A61B 17/6458* (2013.01); *A61B 2017/603* (2013.01)

(58) Field of Classification Search
USPC .................................................. 606/53–59
See application file for complete search history.

(56) References Cited

U.S. PATENT DOCUMENTS

| | | | | |
|---|---|---|---|---|
| 4,135,505 A * | 1/1979 | Day | A61B 17/6466 | 403/110 |
| 4,273,116 A * | 6/1981 | Chiquet | A61B 17/6441 | 403/131 |
| 4,312,336 A * | 1/1982 | Danieletto | A61B 17/6458 | 403/137 |
| 4,554,915 A * | 11/1985 | Brumfield | A61B 17/6425 | 606/54 |
| 4,576,158 A * | 3/1986 | Boland | A61B 17/60 | 606/102 |
| 4,621,627 A * | 11/1986 | DeBastiani | A61B 17/66 | 606/54 |
| 4,628,919 A * | 12/1986 | Clyburn | A61B 17/6491 | 606/55 |
| 4,714,076 A * | 12/1987 | Comte | A61B 17/6458 | 606/57 |
| 4,848,368 A * | 7/1989 | Kronner | A61B 17/66 | 606/57 |
| 4,988,349 A * | 1/1991 | Pennig | A61B 17/6416 | 606/57 |
| 5,122,140 A * | 6/1992 | Asche | A61B 17/6425 | 606/55 |
| 5,160,335 A * | 11/1992 | Wagenknecht | A61B 17/6466 | 606/57 |
| 5,207,676 A * | 5/1993 | Canadell | A61B 17/6491 | 606/54 |
| 5,292,322 A * | 3/1994 | Faccioli | A61B 17/6458 | 606/53 |
| 5,304,177 A * | 4/1994 | Pennig | A61B 17/6416 | 403/374.3 |
| 5,320,444 A * | 6/1994 | Bookwalter | A61B 17/6408 | 248/231.41 |
| 5,320,622 A * | 6/1994 | Faccioli | A61B 17/6491 | 606/58 |
| 5,429,637 A * | 7/1995 | Hardy | A61B 17/6425 | 606/54 |
| 5,620,442 A * | 4/1997 | Bailey | A61B 17/171 | 606/54 |
| 5,662,648 A * | 9/1997 | Faccioli | A61B 17/6458 | 606/53 |
| 5,683,389 A * | 11/1997 | Orsak | A61B 17/6425 | 606/54 |
| 5,688,271 A * | 11/1997 | Faccioli | A61B 17/66 | 606/54 |
| 5,707,370 A * | 1/1998 | Berki | A61B 17/6425 | 606/55 |
| 5,709,681 A * | 1/1998 | Pennig | A61B 17/60 | 606/54 |
| 5,769,851 A * | 6/1998 | Veith | A61B 17/66 | 606/54 |
| 5,788,695 A * | 8/1998 | Richardson | A61B 17/6458 | 606/54 |
| 5,803,924 A * | 9/1998 | Oni | A61B 17/6416 | 606/54 |
| 5,827,282 A * | 10/1998 | Pennig | A61B 17/6458 | 606/54 |
| 5,941,877 A * | 8/1999 | Viegas | A61B 17/6425 | 606/54 |
| 5,951,556 A * | 9/1999 | Faccioli | A61B 17/6458 | 606/64 |
| 6,162,222 A * | 12/2000 | Poka | A61B 17/6433 | 606/54 |
| 6,162,223 A * | 12/2000 | Orsak | A61B 17/6425 | 606/59 |
| 6,171,309 B1 * | 1/2001 | Huebner | A61B 17/6425 | 606/57 |
| 6,217,577 B1 * | 4/2001 | Hofmann | A61B 17/6466 | 606/54 |
| 6,245,071 B1 * | 6/2001 | Pierson | A61B 17/66 | 606/57 |
| 7,004,943 B2 * | 2/2006 | Ferrante | A61B 17/645 | 606/59 |
| D518,174 S * | 3/2006 | Venturini | D24/128 | |
| 7,282,052 B2 * | 10/2007 | Mullaney | A61B 17/6458 | 606/59 |
| 7,758,582 B2 * | 7/2010 | Ferrante | A61B 17/6466 | 606/96 |
| 7,993,069 B2 * | 8/2011 | Persson | B60R 11/0252 | 248/288.51 |
| 8,088,166 B2 * | 1/2012 | Makower | A61B 17/68 | 623/20.14 |
| 8,123,805 B2 * | 2/2012 | Makower | A61B 17/68 | 623/13.12 |
| 8,231,623 B1 * | 7/2012 | Jordan | A61B 17/64 | 606/250 |
| 8,439,914 B2 * | 5/2013 | Ross | A61B 17/62 | 606/54 |
| 9,168,065 B2 * | 10/2015 | Regala | A61F 2/30 | |
| 9,398,957 B2 * | 7/2016 | Landry | A61B 17/56 | |
| 2001/0051806 A1 * | 12/2001 | Ballier | A61B 17/8872 | 606/54 |
| 2002/0013584 A1 * | 1/2002 | Termaten | A61B 17/6425 | 606/54 |
| 2002/0115998 A1 * | 8/2002 | Schoenefeld | A61B 17/6466 | 606/59 |
| 2003/0149429 A1 * | 8/2003 | Ferrante | A61B 17/645 | 606/59 |
| 2003/0225407 A1 * | 12/2003 | Estrada, Jr. | A61B 17/6416 | 606/54 |
| 2004/0097922 A1 * | 5/2004 | Mullaney | A61B 17/6458 | 606/53 |
| 2004/0138659 A1 * | 7/2004 | Austin | A61B 17/6425 | 606/54 |
| 2005/0038425 A1 * | 2/2005 | Werding | A61B 17/6416 | 606/54 |
| 2007/0100338 A1 * | 5/2007 | Deffenbaugh | A61B 17/025 | 606/54 |
| 2007/0123857 A1 * | 5/2007 | Deffenbaugh | A61B 17/025 | 606/54 |
| 2007/0161984 A1 * | 7/2007 | Cresina | A61B 17/6425 | 606/54 |
| 2008/0275509 A1 * | 11/2008 | Clifford | A61B 17/68 | 606/282 |
| 2008/0275562 A1 * | 11/2008 | Clifford | A61B 17/68 | 623/20.21 |
| 2008/0275563 A1 * | 11/2008 | Makower | A61B 17/68 | 623/20.21 |
| 2008/0312656 A1 * | 12/2008 | Vasta | A61B 17/6416 | 606/60 |
| 2010/0249779 A1 * | 9/2010 | Hotchkiss | A61B 17/6425 | 606/59 |
| 2011/0245876 A1 | 10/2011 | Brumfield | | |
| 2012/0150186 A1 * | 6/2012 | Hajianpour | A61B 17/171 | 606/59 |
| 2014/0025076 A1 * | 1/2014 | Lee, Jr. | A61B 17/6466 | 606/59 |
| 2014/0066931 A1 * | 3/2014 | Myers | A61B 17/6458 | 606/59 |
| 2014/0135766 A1 * | 5/2014 | Mingozzi | A61B 17/6425 | 606/59 |
| 2014/0276815 A1 * | 9/2014 | Riccione | A61B 17/6416 | 606/54 |
| 2014/0276824 A1 * | 9/2014 | Cresina | A61B 17/645 | 606/59 |

(56) References Cited

U.S. PATENT DOCUMENTS

| | | | |
|---|---|---|---|
| 2014/0303621 A1* | 10/2014 | Gerold | A61B 17/6458 606/59 |
| 2014/0303622 A1* | 10/2014 | Olsen | A61B 17/6466 606/59 |
| 2014/0350558 A1* | 11/2014 | Triplett | A61B 17/6458 606/59 |
| 2016/0015426 A1* | 1/2016 | Dayton | A61B 17/6416 606/57 |
| 2016/0022315 A1* | 1/2016 | Soffiatti | A61B 17/6416 606/54 |
| 2016/0038184 A1* | 2/2016 | Erickson | A61B 17/6416 606/59 |
| 2016/0151099 A1* | 6/2016 | Olsen | A61B 17/60 606/289 |
| 2016/0157892 A1* | 6/2016 | Zandona' | A61B 17/6458 606/59 |
| 2016/0249952 A1* | 9/2016 | Gerold | A61B 17/6466 |
| 2016/0270822 A1* | 9/2016 | Cresina | A61B 17/62 |

* cited by examiner

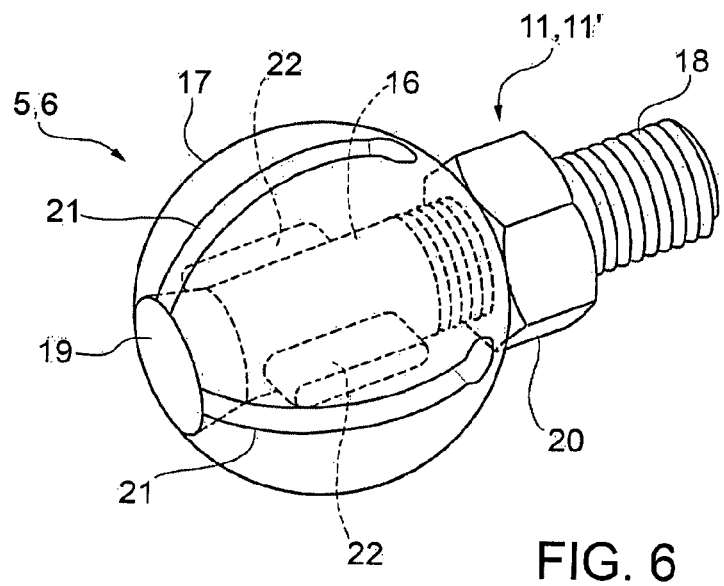
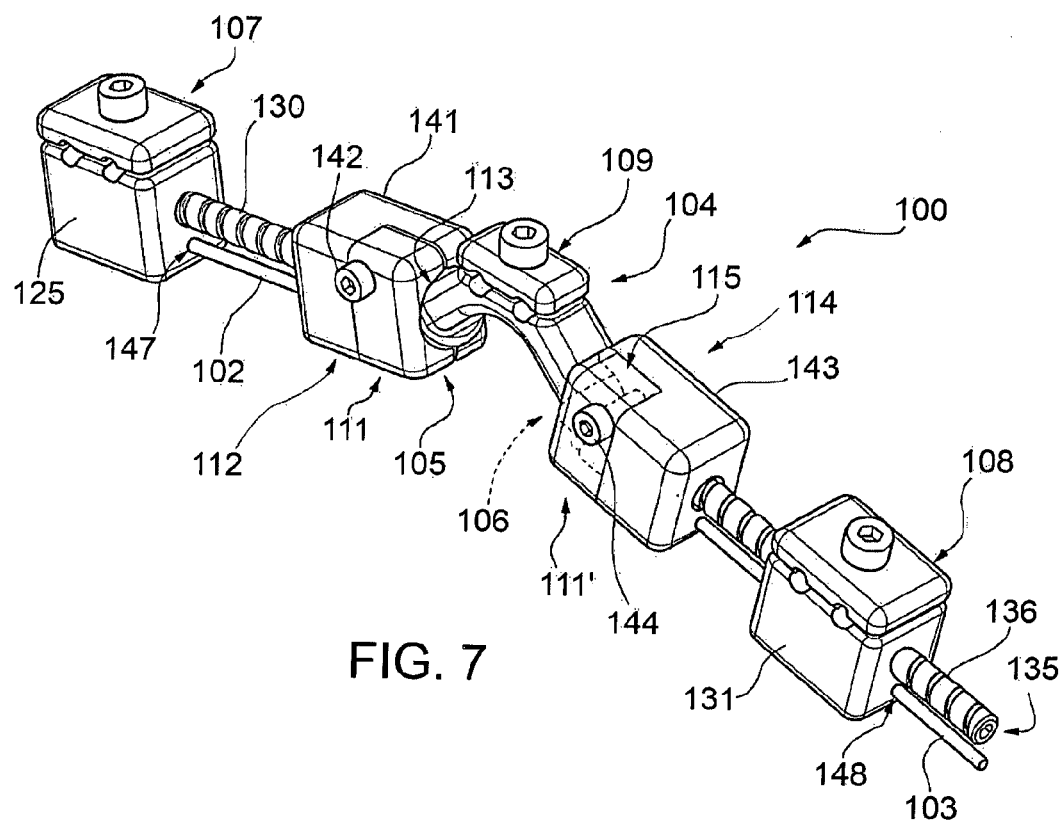

EXTERNAL FIXING DEVICE, FOR TREATING BONE FRACTURES

TECHNICAL FIELD OF THE INVENTION

The present invention refers to an external fixing device for the treatment of bone fractures and, in particular, to an external fixing device, of the articulated type, for the treatment of heel bone fractures.

STATE OF THE ART

External fixing devices are known for the treatment of bone fractures. Such devices allow two fractured bone ends to be kept in the desired position, to promote their correct joining through a natural process known as osteosynthesis. Depending on the configuration of the bone ends to be treated, different types of external fixing devices are available.

With particular reference to the treatment of heel bone fractures, fixing devices are known comprising two or three clamps for connecting the fixing device to predetermined portions of the heel, in order to allow the reduction of the fracture itself and correct positioning of bone fragments.

As known, heel fractures are difficult to treat due to multiple factors including: the shape of the bone, the presence of numerous blood vessels, which supply the portion around the heel, and the presence in such a region of numerous nervous tissues.

Therefore, the surgeon, during the application of a fixing device to the heel, does not always have optimal points available for attaching the device itself to the bone portions to be treated.

In the treatment of simple or limited fractures of the heel fixing devices can be used comprising two connection clamps, the relative position of which can be modified, during the operation.

However, such devices do have as drawback, a field of application limited to simple fractures.

The relative position of the two clamps, indeed, can be varied in space exclusively along a single plane, wherein the two clamps lie, actually limiting the field of application of such a type of fixing device.

If it is necessary to treat more complex heel fractures, it is possible to use external fixing devices comprising three connection clamps. The surgeon, during the operation, can modify the relative position of the three clamps by acting on suitable means for adjusting them, to best adapt the dimensions of the fixing device to the bone portion to be treated.

However, such an embodiment of external fixing device also has the drawback of a limited ability to vary the relative position of the three clamps in space. The clamps, in fact, are moveable along a single plane. Therefore, the relative position of the three clamps can be modified exclusively along such direction.

Such a solution does not make it possible to solve the situation in which it is necessary to position the connection clamps along planes not aligned with each other, precisely because, as stated above, the clamps are mobile within a single plane.

One difficulty encountered by surgeons in the treatment of heel fractures is the limited ability of known fixing devices to vary the position of the connection clamps in space, actually limiting the possibility of adapting the dimensions of the fixing device to the specific dimensions of the heel portion to be treated.

SUMMARY OF THE INVENTION

One object of the present invention is to provide an external fixing device that overcomes the drawbacks described above.

A further object of the present invention is to provide an external fixing device wherein the relative position of the connection clamps can be modified in space, with a large adjustment margin.

Another object of the present invention is to provide an external fixing device in which the adjustment of the relative position of the connection clamps is easy to carry out, in order to reduce the operating time on the patient.

A further object of the present invention is to provide an external fixing device wherein the locking of the clamps, in the position selected by the surgeon, is stable during the application period of the fixing device itself.

In accordance with one aspect of the present invention an external fixing device is provided according to the present specification.

The present specification refers to preferred and advantageous embodiments of the invention.

BRIEF DESCRIPTION OF THE DRAWINGS

Further characteristics and advantages of the present invention shall become clearer from the detailed description of a preferred, but not exclusive, embodiment of an external fixing device for the heel, illustrated as an indication, and not for limiting purposes, in the attached drawing tables, in which:

FIG. 6 is an enlarged perspective view of a component of the external fixing device according to FIG. 5;

FIG. 7 is a perspective view of a further embodiment of the external fixing device according to the present invention;

DETAILED DESCRIPTION OF THE INVENTION

Figure 1:
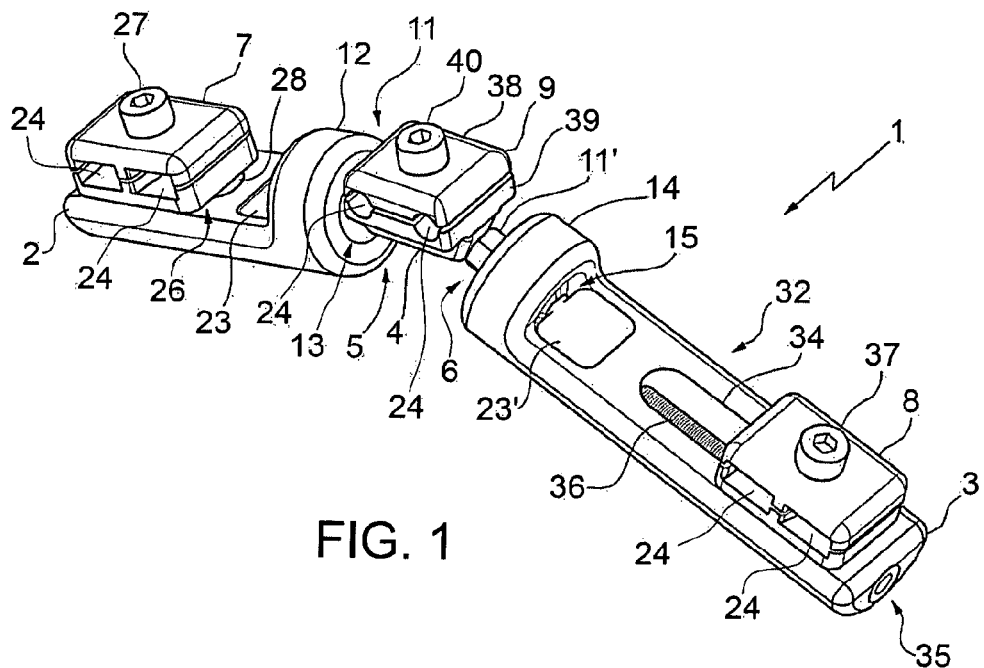
FIG. 1 is a perspective view of an external fixing device according to the present invention.

With reference to the attached figures, reference numeral 1 wholly indicates an external fixing device for the treatment of bone fractures.

In particular, such an external fixing device 1 is foreseen for the treatment of heel bone fractures.

According to further embodiments, such an external fixing device 1 is foreseen for the treatment of fractures of other bone portions.

Moreover, by the term "compression" we mean to indicate the relative bringing together of two bone ends in order to reduce the gap of the fracture between such ends, and by the term "distraction" we mean to indicate the relative moving apart of two bone ends in order to increase the gap of the fracture between such ends.

The fixing device 1, according to the present invention, comprises a first member 2 and a second member 3, having a substantially elongated shape, a central body 4, arranged between the first member 2 and the second member 3, a first ball joint 5, for the articulated connection of the first member 2 to the central body 4, and a second ball joint 6, for the articulated connection of the second member 3 to the central body 4.

The fixing device 1 also comprises a first clamp 7, associated in a movable manner with the first member 2, a second clamp 8, associated in a movable manner with the second member 3 and a third clamp 9, associated with the central body 4 at the top thereof.

The first clamp 7, the second clamp 8 and the third clamp 9 are suitable for housing pins or screws or similar known elements, to ensure the connection of the fixing device 1 to the bone portions to be treated.

Through the first ball joint 5 and the second ball joint 6 it is possible to respectively modify the position of the first member 2 and/or of the second member 3 with respect to the central body 4, along a substantially unlimited number of directions.

Figure 2:
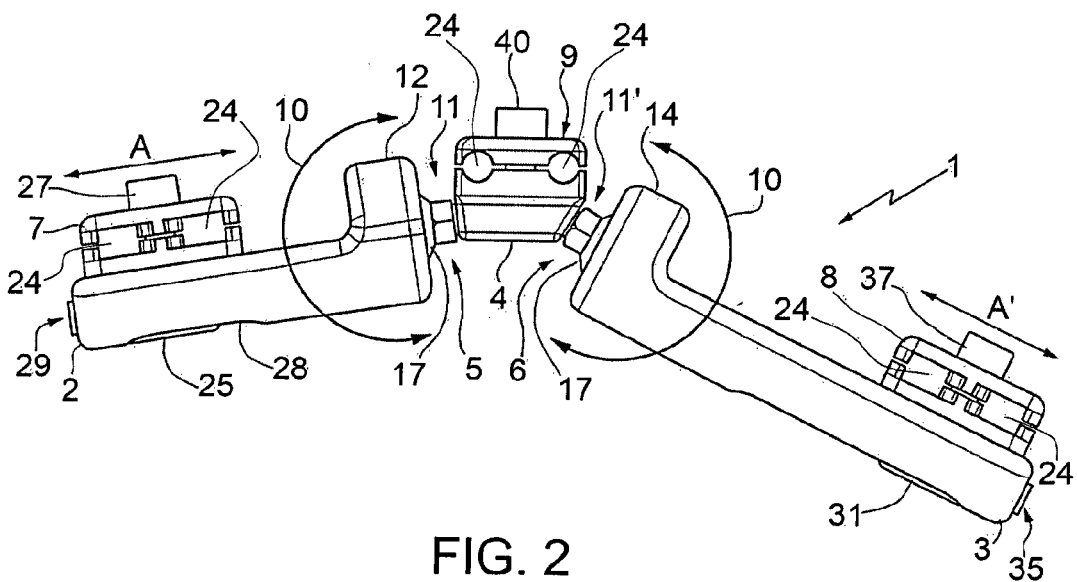
FIG. 2 is a front view from above of the external fixing device according to FIG. 1.
Figure 3:
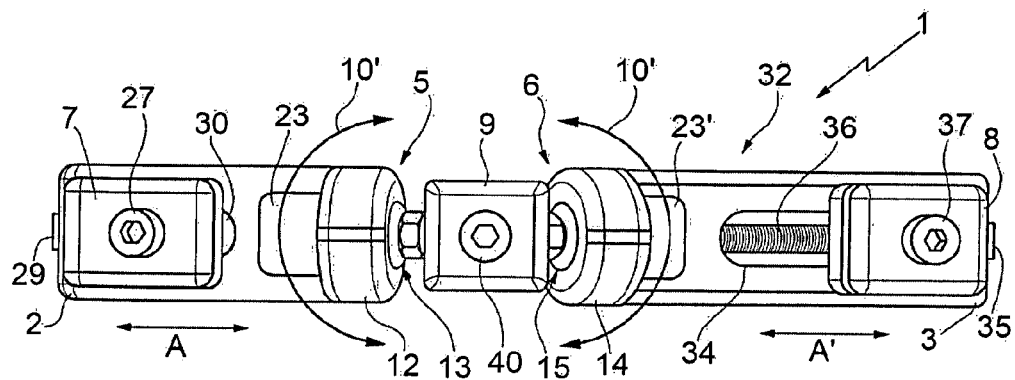
FIG. 3 is a view from above of the external fixing device according to FIG. 1.
Figure 4:
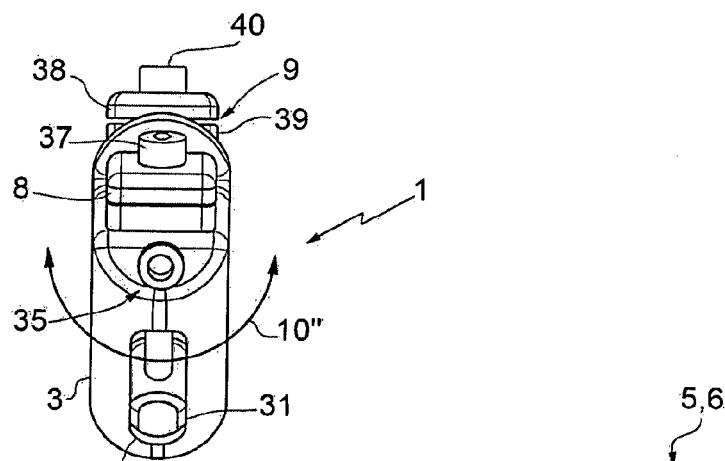
FIG. 4 is a side view of the external fixing device according to FIG. 1.

With reference to the embodiment of the fixing device 1 shown in FIGS. 2-4, the directions lying on three planes, orthogonal with one another, along which it is possible to direct the first member 2 and/or the second member 3 with respect to the central body 4, are illustrated through the arrows 10, 10', 10", as a non-limiting example.

Therefore, it is possible to direct the first clamp 7 with respect to the third clamp 9 in an articulated manner along at least the aforementioned planes 10, 10', 10" that are perpendicular to one another.

Similarly, it is possible to direct the second clamp 8 with respect to the third clamp 9 along at least the aforementioned planes 10, 10', 10".

In this way, it is possible to obtain a substantially unlimited number of assembly configurations of the fixing device 1 itself.

Once the configuration of the fixing device 1 most closely matching the location of the fracture to be treated has been obtained, it is possible to lock the relative position of the first member 2 with respect to the central body 4 by acting on locking means 11.

Such locking means 11 are operatively associated with the first ball joint 5 as described more clearly hereafter.

Similarly, it is possible to lock the relative position of the second member 3 with respect to the central body 4 by acting on locking means 11', operatively associated with the second ball joint 6.

The locking means 11 and 11' are equal to each other and, therefore, hereinafter only the locking means 11 will be described.

The first member 2, at one end 12, has a seat 13 for housing the first ball joint 5. In particular, after having connected the first member 2 to the first ball joint 5, the end 12 faces the central body 4 itself.

The seat 13 can have a hollow spherical, hemispherical or similar shape or, in general, a shape suitable for housing the spherical end of the first joint 5.

Similarly, the second member 3, at one end 14, has a seat 15 for housing the second ball joint 6.

The end 14, after the connection of the second member 3 to the second ball joint 6, faces the central body 4.

The first ball joint 5 and the second ball joint 6 have the same structure. Accordingly, hereinafter the structure of the first ball joint 5 only will be described, with it being understood that the corresponding elements present in the second ball joint 6 will be illustrated in the figures with the same reference numerals.

In a version of the present invention, illustrated in FIGS. 1-6, the first ball joint 5 comprises an elongated element 16, having a substantially cylindrical shape, partially housed inside a spherical element 17, in a through opening obtained in the latter for this purpose, and in which such an elongated element 16 is movable with respect to the latter.

FIG. 6 illustrates the elongated element 16 that is coaxial to the spherical element 17 and extends outward from a portion only of the latter.

Equivalent versions of the position of the elongated element 16 can be foreseen, without departing from the scope of protection of the present invention.

Along the elongated element 16, and in particular along at least the portion extending outward from the spherical element 17, a threading 18 is formed, suitable for allowing the removable connection of the first ball joint 5 to the central body 4 or to the component to which it is connected. In particular, the threaded portion 18 can be associated with a corresponding threaded seat formed in the central body 4 or in the element to which it is connected, not illustrated in the figures.

The elongated element 16, at the end arranged inside the spherical element 17, has an enlarged portion 19.

The enlarged portion 19, which for example has a frusto-conical or similar shape, has at least one larger cross section with respect to a cross section of the through opening of the spherical element 17 and is suitable for determining the symmetrical radial expansion of the spherical element 17, thus causing the relative locking between the first member 2 and the central body 4 and/or between the second member 3 and the central body 4.

Due to such a radial expansion, the outer surface of the spherical element 17 is arranged partially or completely in abutment against the inner surface of the seat of the first member 2.

Based on the extent of the radial expansion of the element 17 it is possible to vary the degree of interference between the outer surface of the spherical element itself and the inner surface of the respective seat, partially limiting or completely blocking the mobility of the ball joint 5.

The configuration of the widened portion 19 of the insert is advantageously different from the configuration of the through opening at such a portion 19. This is advantageous since the contact area between the elongated element 16 and the through opening, and therefore the friction between them, is reduced, thus making it easier for the elongated element 16 to slide in the spherical element 17 both in one direction and in the other. Moreover, since the radial expansion of the spherical element 17 is substantially symmetrical, the spherical element 17 goes into abutment uniformly against the respective seat in the first member 2, ensuring a stable and secure locking of the ball joint 5.

After having connected the first member 2 to the central body 4 through the first ball joint 5, the surgeon can lock their relative movement by acting on the locking means 11, as described better hereinafter.

The locking means 11 comprise at least one adjustment nut 20, associated with the threaded portion 18 of the elongated element 16.

Figure 5:
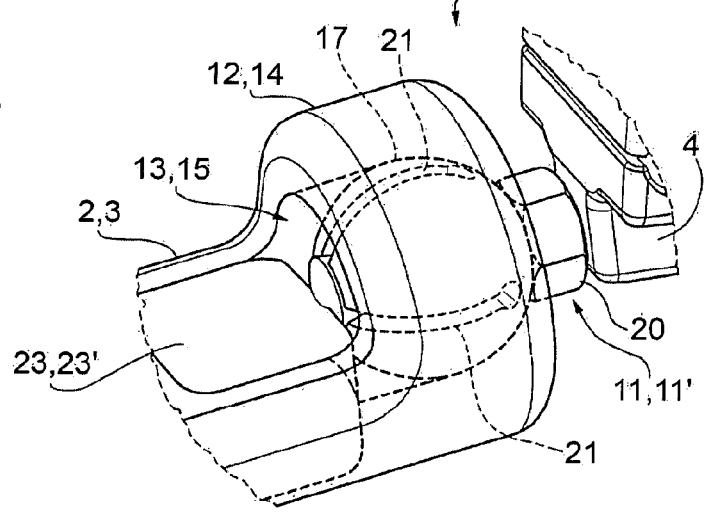
FIG. 5 is an enlarged view of a detail of the external fixing device according to FIG. 1.
Figure 8:
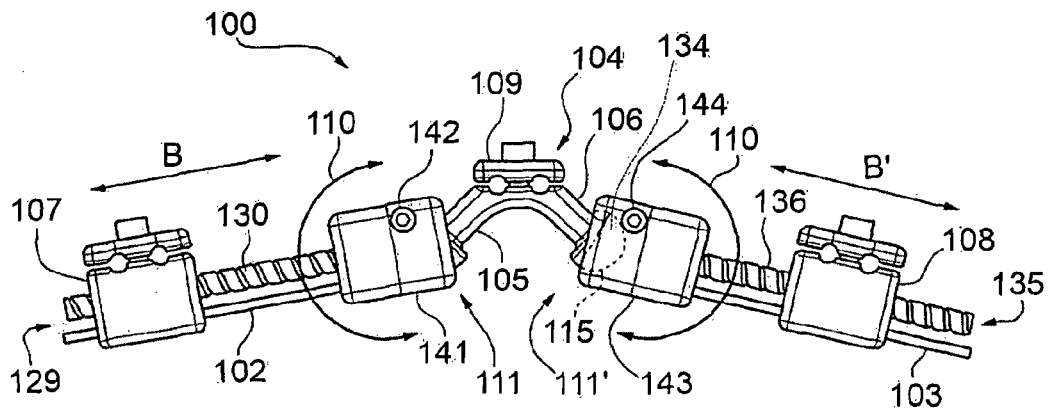
FIG. 8 is a front view of the external fixing device according to FIG. 7.
Figure 9:
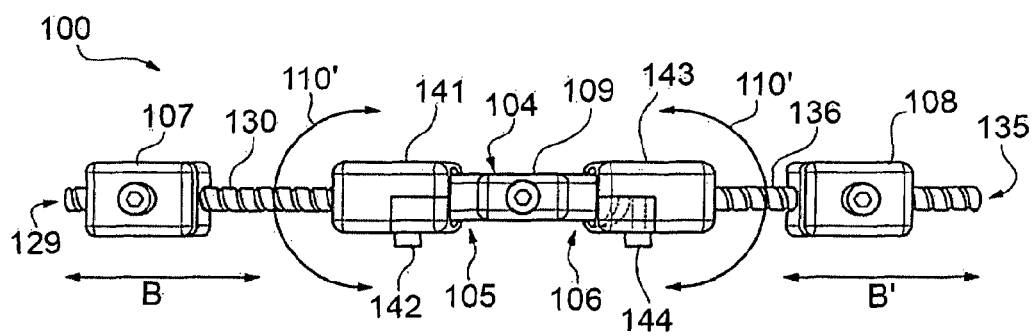
FIG. 9 is a view from above of the external fixing device according to FIG. 7.
Figure 10:
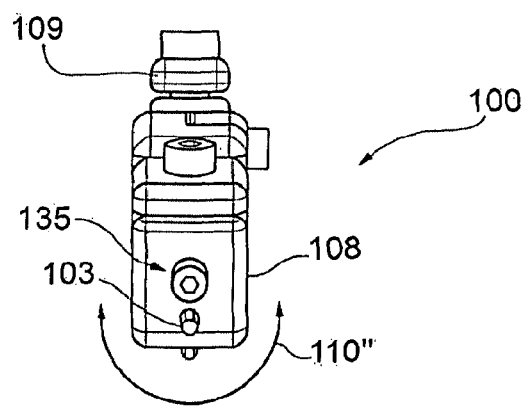
FIG. 10 is a side view of the external fixing device according to FIG. 7.

As illustrated in FIG. 5, after having connected the first ball joint 5 to the central body 4, the at least one adjustment nut 20 is arranged between the spherical element 17 and the central body 4 itself.

The spherical element 17 has at least one radial notch 21, suitable for allowing the radial expansion of the spherical element 17 itself.

Preferably, at least one notch 21 is provided, of the radial type, suitable for allowing a substantially symmetrical radial expansion of the spherical element 17 itself.

For example, there can be two diametrically opposite notches 21, designed to obtain a substantially symmetrical radial expansion of the spherical element 17 itself. The spherical element 17 can also have a different number of equally angularly spaced notches, for example 3 or 4 as illustrated in FIG. 6.

After having connected the first ball joint 5 to the central body 4 and then the first member 2 to the first joint 5, it is possible to lock the mobility of the first joint 5 itself by acting on the adjustment nut 20, thereby constraining the first member 2 to the central body 4.

By acting on the adjustment nut 20, in fact, the enlarged portion 19 of the elongated element 16 is moved forwards inside the spherical element 17, causing the radial expansion of the latter.

By expanding, the spherical element 17 goes into abutment against the seat 13 of the first member 2, actually preventing the relative rotation between the first member 2 and the central body 4.

By acting on the adjustment nut 20, in the opposite way, the outer diameter of the spherical element 17 is reduced, restoring the mobility of the first ball joint 5.

In order to obtain a correct centring of the elongated element 16 with respect to the spherical element 17, and thus ensure a substantially symmetrical radial expansion of the spherical element 17, at least one guide element 22 is provided, or in particular at least one pair of guide elements 22, which project from the elongated element 16 and are slidably engaged in the at least one notch 21.

As shown in the embodiment illustrated in FIG. 6, the guide elements 22 comprise two tabs projecting diametrically from the elongated element 16. However, further embodiments are possible, wherein the guide elements 22 are pin shaped or similar, suitable for sliding along the at least one notch 21.

The guide elements 22 acts as guides for the elongated element 16 with respect to the spherical element 17, avoiding the rotation of the elongated element 16 inside the spherical element 17, ensuring a centring of the elongated element 16 with respect to the spherical element 17 and a substantially symmetrical radial expansion of the latter. Lastly, in order not to obstruct the relative rotation of the spherical element 17 inside the seat 13, during the positioning of the first member 2, the guide elements 22 are completely inside the spherical element 17.

By acting in an analogous way to what has been described earlier relative to the first ball joint 5, it is possible to modify and lock the relative position of the second member 3 with respect to the central body 4 by acting on the locking means 11' of the second ball joint 6.

In particular, by acting on the adjustment nut 20 associated with the second ball joint 6 the radial expansion/contraction of the spherical element 17 inside the seat 15, formed in the second member 3, is caused, thereby allowing/blocking the mobility of the second member 3 itself with respect to the central body 4.

In a further version of the present invention, in order to ensure that the spacer device 1 has a further degree of freedom in the adjustment of the position of the first member 2, with respect to the central body 4, it is foreseen to use at least one shim element 23 to be housed inside the seat 13.

The at least one shim element 23 is foreseen to be arranged between the first member 2 and the first joint 5.

In particular, the at least one thickness 23 is housed in the seat 13 and thus arranged between the latter and the spherical element 17 of the first joint 5.

Accordingly, the at least one shim element 23, by reducing the inner space of the seat 13, causes the spherical element 17 to move forward towards the outside of the seat 13 itself, thus increasing the distance between the first member 2 and the central body 4.

Similarly, it is possible to modify the position of the second member 3 with respect to the central body 4 through at least one shim element 23', housed in the seat 15 of the second member 3.

The fixing device 1 is connected to the bone portions to be treated by means of the clamps 7, 8, 9.

The first clamp 7, the second clamp 8 and the third clamp 9 each have an upper portion removably associated with a lower portion, in order to allow the housing and then the fastening of pins, screws or similar elements for connecting the external fixing device 1 to bone portions to be treated, according to methods known in the field.

For this purpose, the first clamp 7, the second clamp 8 and the third clamp 9 each have at least one pair of seats 24 wherein to pins, screws or similar elements, not illustrated in the figures can be housed.

The first clamp 7 is associated in a mobile manner with the first member 2, in a longitudinal direction.

In particular, the first clamp 7 comprises a base 25. An attachment screw 27 is also provided which connects the first clamp 7 to the base 25.

The first clamp 7 is removably associated with the base 25 through the attachment screw 27.

The attachment screw 27, therefore, allows the removable connection between an upper portion of the clamp 7 and a lower portion thereof, according to methods known in the art.

By acting on the attachment screw 27, it is possible to loosen the first clamp 7 from the base 25 and then rotate it about a vertical axis, corresponding to that of the screw 27, not shown in the figures. In this way, the orientation of the clamp 7 is modified with respect to the longitudinal direction of the first member 2 and/or of a linear guide 26, formed in the first member 2, in the longitudinal direction, thereby varying the orientation of the pins or of the attachment screws to be applied to the bone portion to be treated.

The first clamp 7, and/or in particular the base 25 thereof, is slidably associated along the linear guide 26.

The linear guide 26 comprises a seat 28, for example a slot or a recess passing through the first member 2, formed in the longitudinal direction along the first member 2, and means 29 for adjusting the position of the first clamp 7 along the first member 2.

The adjustment means 29 comprise an adjustment screw 30, oriented in the longitudinal direction along the first member 2, associated, with a screw-and-nut type coupling, with the base 25 of the first clamp 7.

Therefore, by rotating the adjustment screw 30 the first clamp 7 is made to move along the first member 2.

The second clamp 8 is associated in a mobile manner with the second member 3 in an analogous way to what has been described above regarding the connection of the first clamp 7 to the first member 2.

In particular, the second clamp 8 comprises a base 31 slidably associated along a linear guide 32 formed along the second member 3, in the longitudinal direction.

The linear guide 32 comprises a seat 34, formed along the second member 3 and means 35 for adjusting the position of the second clamp 8 along the second member 3.

The adjustment means 35, which are analogous to the adjustment means 29 of the first clamp 7, comprise an adjustment screw 36, oriented in the longitudinal direction along the second member 3, and associated, by a coupling of the screw-and-nut type, with the base 31 of the second clamp 8.

Therefore, by rotating the adjustment screw 36 the movement of the second clamp 8 along the second member 3 is obtained.

The second clamp 8 is removably associated with the base 31 through an attachment screw 37, similarly to what has been described above for the first clamp 7.

By acting on the attachment screw 37, it is possible to modify the orientation of the second clamp 8 about a substantially vertical axis, not shown in the figures, thus varying the orientation of the pins or of the attachment screws to be applied to the bone portion to be treated.

Therefore, since it is possible to modify the relative position of the first clamp 7 along the first member 2 and/or of the second clamp 8 along the second member 3, the surgeon is able, if needed, to carry out a distraction or a compression of the bone ends to be treated.

Moreover, the surgeon is able to rotate the first clamp 7 and/or the second clamp 8 about respective vertical axes, and he is able to adapt the orientation of the connection pins and thus the configuration of the fixing device 1 to the shape of the bone portion to be treated.

The third clamp 9, similarly to the first clamp 7 and to the second clamp 8, comprises an upper portion 38 and a lower portion 39.

In a version of the present invention, illustrated in FIGS. 1-4, the lower portion 39 is fixedly connected to the central body 4, whereas the upper portion 38 is removably connected to the lower portion 39 through an attachment screw 40.

In a further version, not shown in the figures, the upper portion 38 and the lower portion 39 are removably connected to the central body 4 through the attachment screw 40. Therefore, similarly to what has been described above for the first clamp 7 and the second clamp 8, it is possible to vary the orientation of the third clamp 9 by rotating it about a vertical axis, corresponding to that of the screw 40, not shown in the figures.

The presence of a third clamp 9, at the central body 4, allows the effective use of the fixing device 1 for the treatment of any type of heel bone fracture, both in the case of simple bone fractures and in the case of complex bone fractures.

The fixing device 1, according to the present invention, indeed, has a first clamp 7, a second clamp 8 and a third clamp 9 which can be articulated with respect to one another substantially into any reciprocal position in space. In particular, the third clamp 9 acts as a reference element for the connection of the fixing device 1 to the site to be treated.

The first clamp 7 and the second clamp 8, moreover, being articulated to the third clamp 9 through a first ball joint 5 and a second ball joint 6, can be positioned substantially in any position in space, thus ensuring the possibility of adapting the dimensions of the external fixing device 1 to any type of heel fracture to be treated. FIGS. 7-10 show a further embodiment of an external fixing device according to the present invention, wholly indicated with reference numeral 100.

Hereafter, the elements corresponding to those described above are indicated with the same reference numeral increased by one hundred.

The fixing device 1 comprises a first member 102, a second member 103, a central body 104, arranged between the first member 102 and the second member 103.

The central body 104 comprises a first substantially ball-shaped joint 105, for the articulated connection of the first member 102 to the central body 104 and a second substantially ball-shaped joint 106, for the articulated connection of the second member 103 to the central body 104. The fixing device 100 also comprises a first clamp 107, associated in a mobile manner with the first member 102, a second clamp 108, associated in a mobile manner with the second member 103 and a third clamp 109, associated at the top with the central body 104.

Similarly to what has been described for the previous embodiment, the first clamp 107, the second clamp 108 and the third clamp 109 are suitable for housing pins, screws or similar known elements, not illustrated in the figures, to secure the connection of the fixing device 100 to the fractured bone portion to be treated.

The fixing device 100 differs from the previous embodiment in the configuration of the first and second ball joints 105 and 106 and in the configuration of the relative locking means 111, 111' to the first member 102 and to the second member 103, respectively.

The first member 102 and the second member 103 have an elongated shape, for example cylindrical, prismatic or similar.

The first member 102, at one end 112, has a prismatic portion 141.

The end 112, after the connection of the first member 102 to the central body 104, faces the central body 104 itself.

At the prismatic portion 141 a hollow seat 113 is formed, for the connection of the first ball joint 105 to the first member 102.

The hollow seat 113 is a portion of a ball, and it allows the spherical end of the first ball joint 105 to be housed therein.

The first ball joint 105 is connected to the first member 102 through locking means 111.

The locking means 111 have a hollow seat 143, shaped like a ball portion, and they are removably associated with the prismatic portion 141, through at least one screw 142.

The locking means 111 comprise for example a cover portion delimiting the hollow seat 143.

By associating the locking means 111 with the prismatic portion 141, the hollow seats 113 and 143 make a substantially spherical seat in which to house the spherical end of the first ball joint 105.

By acting on the screw 142 the locking means 111 are brought into abutment against the spherical end of the first ball joint 105, actually blocking the mobility thereof inside the seat 113.

In this way, it is possible to allow/prevent the mobility of the first member 102 with respect to the central body 104.

The second member 103 is connected to the central body 104 through a second ball joint 106, which is shaped analogously to the first ball joint 105.

The second member 103, at one end 114, has a prismatic element 143. In particular, the end 114, after having connected the second member 103 to the central body 104 through the second ball joint 106, faces towards the central body 104.

The prismatic element 143 comprises a seat 134 shaped like a ball portion, for housing the spherical end of the second ball joint 106.

The second ball joint 106 is connected to the second member 103 through locking means 111'.

The locking means 111', which are configured analogously to the locking means 111, are removably associated with the prismatic portion 143 of the second member 103 through at least one screw 144.

The locking means 111' have a hollow seat 146 shaped like a ball portion. The locking means 111' comprise for example a cover portion delimiting the hollow seat 146. Therefore, by associating the locking means 111' with the prismatic portion 143, the hollow seats 134 and 146 make a substantially spherical seat in which to house the spherical end of the second joint 106.

The operation of the locking means 111' is the same as that of the means 111 and therefore it will not be described any further.

Moreover, the present embodiment of a fixing device 100 also allows the relative position of the first clamp 107 with respect to the third clamp 109 to be modified along three planes perpendicular to one another, indicated in the figures by 8 and 10, through the arrows 110, 110', 110".

The first clamp 107, indeed, is associated with the first member 102 that is connected in an articulated manner to the central body 104 through the first ball joint 105.

Similarly, through the connection of the second member 103 to the central body 104 by means of the second ball joint 106, it is possible to orient the second clamp 108 with respect to the third clamp 109 along the aforementioned three directions 110, 110', 110".

The first clamp 107 is slidably associated with the first member 102, along a longitudinal direction B.

In particular, the first clamp 107 has a base 125 equipped with a through opening 147 in which the first member 102 is inserted.

The configuration of the through opening 147 corresponds to that of the first member 102. In this way, a precise mobile connection is made between the first member 102 and the first clamp 107.

The position of the first clamp 107 along the first member 102 is adjusted through adjustment means 129.

The adjustment means 129 comprise an adjustment screw 130, arranged parallel to the first member 102.

The adjustment screw 130 is associated with one end of the prismatic portion 141, with a worm screw type connection and, on the opposite side, with the base 125 of the first clamp 107 with a coupling of the screw-and-nut type.

Therefore, by rotating the adjustment screw 130 there is a movement of the first clamp 107 along the first member 102.

The second clamp 108 is slidably associated with the second member 103 in an analogous manner to what has been described above for the first clamp 107.

In particular, the second clamp 108 comprises a base 131 equipped with a through opening 148 in which the second member 103 is housed.

The configuration of the through opening 148 corresponds to that of the second member 103. In this way, there is a precise mobile connection between the second member 103 and the second clamp 108.

Therefore, the second clamp 108 is slidably associated with the second member 103 through adjustment means 135, comprising an adjustment screw 136. The adjustment screw 136 is associated at one end with the prismatic portion 143 of the second member 103, with a coupling of the worm screw type, and with the base 131 of the second clamp 108 with a coupling of the screw-and-nut type.

Therefore, by rotating the adjustment screw 136 the movement of the second clamp 108 along second member 103 is obtained.

FIGS. 11 to 15 illustrate a further embodiment of an external fixing device according to the present invention, wholly indicated with reference numeral 200.

The fixing device 200, similarly to the previous embodiments, comprises a first member 202, a second member 203, and a central body 204 arranged between the first and the second member 202 and 203.

The fixing device 200 comprises a first ball joint 205, for the articulated connection of the first member 202 to the central body 204 and a second ball joint 206, for the articulated connection of the second member 203 to the central body 204.

The first ball joint 205 and the second ball joint 206 can be removably connected to the central body 204.

The fixing device 200, similarly to the previous embodiments, comprises a first clamp 207, associated in a mobile manner with the first member 202, a second clamp 208, associated in a mobile manner with the second member 203 and a third clamp 209, associated at the top with the central body 204, each clamp being suitable for housing one or more pins, screws or similar known elements, not illustrated in the figures, to secure the connection of the fixing device 200 to the fractured bone portion to be treated.

The fixing device 200 differs from the previous embodiments in the configuration of the first ball joint 205 and of the second ball joint 206 and in the configuration of the first and second member 202 and 203 at the housing seats of the respective joints.

Moreover, the fixing device 200 differs from the previous embodiments in terms of the configuration of the locking means 211, 211' of the first ball joint 205 and of the second ball joint 206, at the first and second member 202 and 203, respectively, as will be more clearly described hereinafter.

The first member 202 and the second member 203 have a configuration similar to that of the first member 2 and of the second member 3.

The first member 202, at one end 212, has a seat 213 for housing the first ball joint 205 configured substantially like a spherical cap that will be discussed further hereafter. In particular, the end 212 of the first member, after the connection of the first member 202 to the first ball joint 205 faces the central body 204.

Similarly, the second member 203, at one end 214, has a seat 215 for housing the second ball joint 206 with an analogous configuration to that formed in the first member 203.

The first ball joint 205 and the second ball joint 206 have the same configuration. Therefore, hereinafter the configuration of the first ball joint 205 only will be described, with it being understood that the corresponding elements present in the second ball joint 206 will be illustrated in the figures with the same reference numerals.

Figure 13:
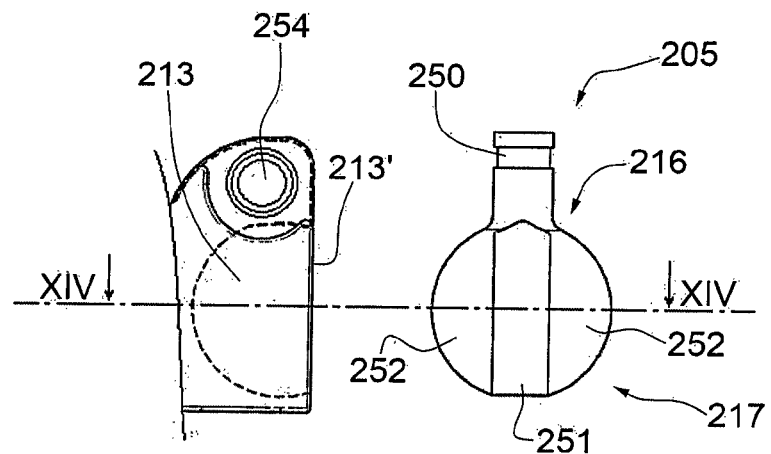
FIG. 13 shows a front view with separated components of a detail of the external fixing device according to the present invention.
Figure 14:
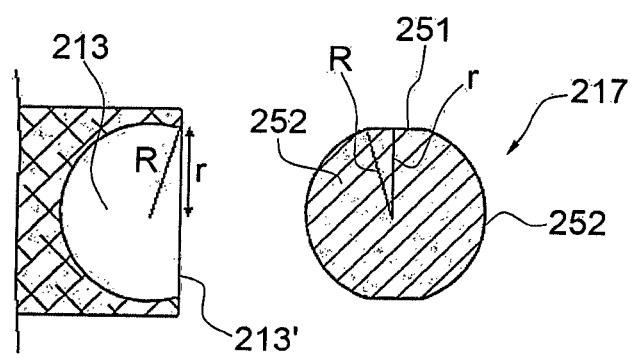
FIG. 14 is a section view of the detail of the external fixing device illustrated in FIG. 13, taken along the line XIV-XIV of FIG. 13.

With reference in particular to FIGS. 13 and 14, the first ball joint 205 comprises a substantially ball-shaped spherical element 217 from which an elongated element 216 projects. The elongated element 216 is constrained to the spherical element 217.

The spherical element 217 comprises a substantially cylindrical central portion 251, arranged between two substantially spherical cap-shaped portions 252. The spherical element 217 is sized so that the circular base of each substantially spherical cap-shaped portion 252 matches with a respective base of the substantially cylindrical portion 251. The spherical element 217 can be obtained either in a single piece, for example by milling of a portion of the outer surface of the spherical element itself, or through assembly, in a way known to the man skilled in the art, of many separate components. The elongated element 216, as stated above, has an elongated configuration and rises up radially from the spherical element 217 at the side face of the substantially cylindrical portion 251. Indeed, in the substantially cylindrical portion 251 there is a radial housing seat, for example threaded, for a respective portion (not illustrated in the figures) of the elongated element 216, on which a threading of corresponding pitch is formed. In any case, the engagement between the elongated element 216 and the spherical element 217 can be made through equivalent engagement means, for example of the snap-insertion type or other similar ones or the elongated element can be made in a single piece with the spherical element 217.

The substantially cylindrical central portion 251, at the circular cross section thereof, has a smaller radius r with respect to the radius of curvature R of each substantially spherical cap-shaped portion 252 (see in particular FIG. 14), so that the spherical element 217 has smaller overall dimensions in a plane parallel to the bases of such a substantially cylindrical central portion 251.

The free end of the elongated element 216, which has for example a cylindrical configuration, is designed to be inserted, in use, inside a corresponding seat, formed in the central body 204. For this purpose, accordingly, an annular recess 250 can be formed on the elongated element 216, for the engagement with corresponding engagement means provided for this purpose in the central body 204. Other configurations of the engagement means, known to the man skilled in the art, can, in any case, be foreseen. The elongated element 216 can for example comprise a threaded portion designed to be screwed/unscrewed into/from a corresponding seat provided in the central body 204, which is in turn threaded with the same threading pitch.

As it can be seen, the configuration of the elongated element 216 according to such an example embodiment is very simple.

A ball joint 205 of this type is foreseen to be housed in a respective hollow housing seat 213, formed in the first member 202 at an end thereof 212. Such a hollow housing seat 213 has a substantially spherical cap-shaped configuration with a radius of curvature slightly greater than the radius of curvature R of the substantially cap-shaped portions 252 of the spherical element 217 and delimiting an inlet mouth 213' with a substantially circular configuration having a radius slightly larger than the radius r of the circular section of the substantially cylindrical central portion 251 but smaller than the radius of curvature R of the substantially cap-shaped portions 252.

The hollow housing seat 213 shaped substantially like a spherical cap delimits a region of volume at least equal to half the spherical element 217 of the joint 205.

The hollow seat 213 is open on top (opening 213") so as not to interfere with the elongated element 216 of the ball joint 205 when it is inserted in the seat 213. At such an upper opening 213" and at opposite sides thereof, the first member 202 has two plates of a jaw-type end 255 designed, as outlined more clearly hereinafter, to lock/fasten in position the spherical element 217 of joint 205 in the seat 213.

Advantageously, the substantially cap-shaped housing seat 213 will be sized so that, once the spherical element 217 of the joint 205 has been locked in position, it is uniformly in abutment on the surface of the substantially cap-shaped portions 252 of the spherical element, thus ensuring a large engagement surface between the spherical element 217 and the seat 213.

In other words, the housing seat 213 in its attachment configuration has a geometric shape, which for example can be that of a spherical seat, corresponding exactly to that of the spherical element of the joint 205. With such a configuration the ball joint 205 can be inserted in the respective seat 213 only when arranged with the bases of the cylindrical portion 251 parallel to the inlet mouth 213' and the elongated element 216 aligned with the opening 213" between the two plates.

The ball joint 205 according to the present embodiment of the invention comprises locking means 211, intended, in use, to prevent the rotation of the spherical element 217 of the joint 205 once it is inserted in the respective seat 213.

Such locking means 211 comprise, for example, clamping means of the two plates of the jaw-type end 255, for example a screw 253 able to be screwed/unscrewed into/from corresponding threaded seats 254 formed for this purpose in the aforementioned plates.

Once the spherical element 217 of the joint 205 has been inserted in the respective seat 213 and the spherical element itself has been rotated into the desired position, by screwing the screw 253 into the respective seats 254 the plates of the jaw-type element 255 are clamped together and there is a consequent reduction in the housing seat 213 that is sufficient, as explained above, to obtain the effective locking of the spherical element 217 in the desired position.

Advantageously, in order to keep the locking means 211 within the bulk of the first component 202, the plate-like portion of the jaw-type end 255 in contact, in use, with the head of the screw 253, will have a low thickness.

Optionally, it is possible to provide a notch or mark on the screw 253 intended to indicate to the operator, during the locking of the joint 205 in the respective seat 213, the correct clamping together of the two plates of the jaw-type end 255.

The elongated element 216 is foreseen to be inserted inside a corresponding seat, not illustrated in the attached figures, formed in the central body 204. More particularly, the central body 204, at opposite sides thereof, comprises at least one engagement seat with the elongated element 216, in order to ensure the connection of at least one first member 202 with a second member 203.

According to a version of the present invention, the connection between the central body 204 and the elongated element 216 of the first and second ball joint 205 and 206 is either of the fixed type (as for example illustrated in FIG. 7 with reference to the fixing device 100) or removable.

As a non-limiting example, the connection between the first ball joint 205 and the central body 204 can take place through interlocking means, not illustrated in the figures, of the type known in the field and therefore not described any further.

In particular, the interlocking means can engage in the annular seat 250 (FIG. 12) obtained on the elongated element 216, for example close to the free end thereof.

As far as the connection between the first ball joint 205 and the first member 202 is concerned, reference is made to the example scheme illustrated in FIG. 13.

The connection between the second joint 206 and the second member 203 occurs accordingly and, therefore, it will not be described any further.

In the initial configuration A, the first member 202 and the first ball joint 205 are separate from one another. For the interlocking of the first ball joint 205 inside the seat 213 formed in the first member 202 the joint is positioned so that the elongated element 216 is aligned with the upper opening 213" comprised between the plates of the jaw-type end 255, and so that the substantially cylindrical central portion 251 has its circular bases arranged parallel to the inlet mouth 213' of the seat 213 (FIGS. 13, 14 and 15—configuration A).

The ball joint 205 is then inserted inside the seat 213 (FIG. 15—configuration B) and the elongated element 216 of the joint 205 is taken into the desired position. It should be noted that as soon as the ball joint 205 is moved in the seat with respect to its insertion position, for example by angularly moving the elongated element 216 downwards (FIG. 15—configuration C), the spherical element 217 of the joint 205 remains engaged in the seat itself, since the seat itself and the inlet mouth 213' are of dimensions such as to prevent it from coming out.

Figure 15:
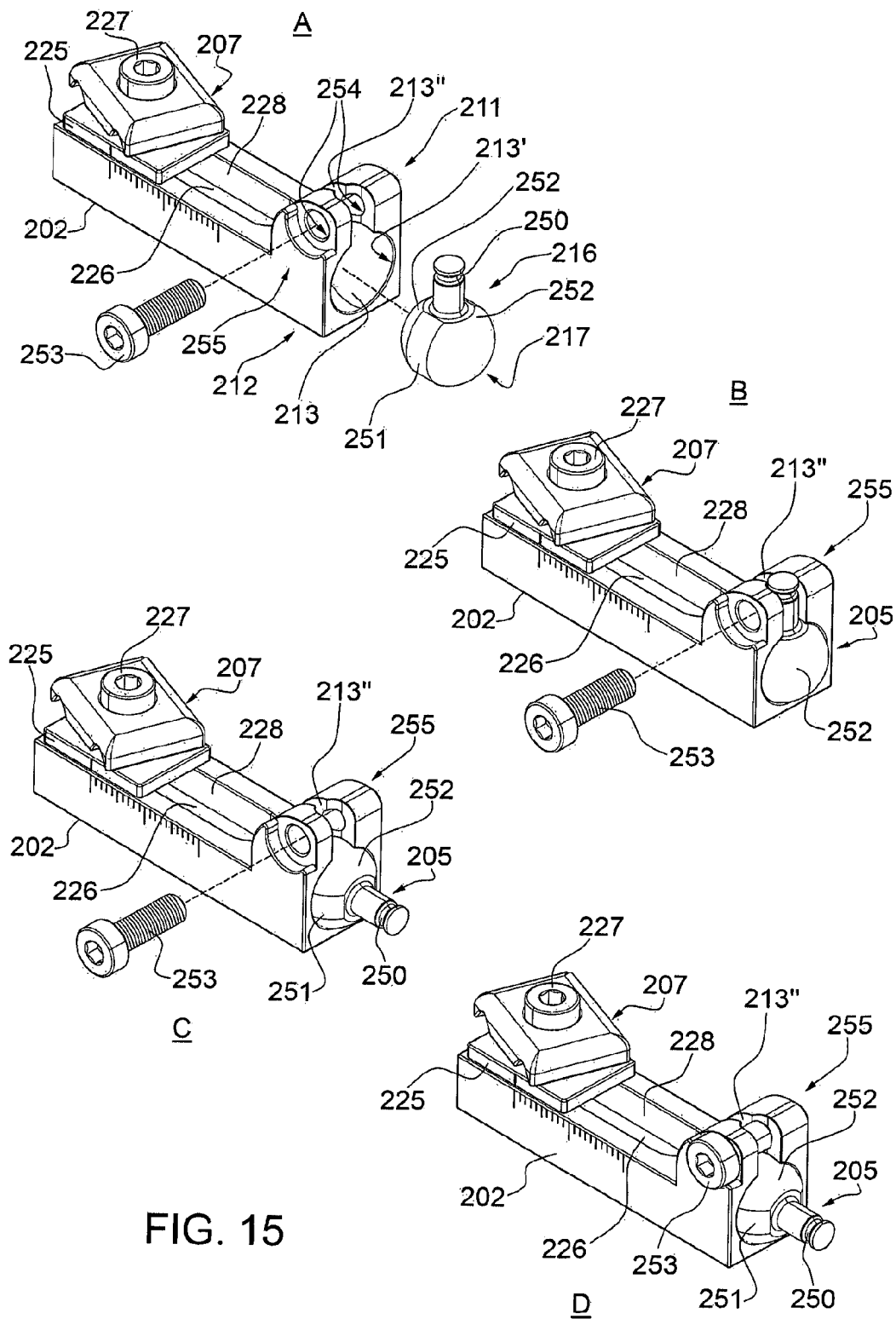
FIG. 15 is a simplified scheme of the assembly steps/configurations of a detail of the fixing device according to FIG. 12.

Accordingly, once the joint 205 has been brought into the desired position, in order to block its rotation inside the seat 213 the screw 253 is inserted and screwed inside the threaded seats 254, clamping together the plates of the jaw-type end 255 (FIG. 15—configuration D).

In this way, the compression of the jaw-type end 255 causes a reduction of the housing seat 213, which is sufficient to cause the uniform engagement between the substantially cap-shaped portions 252 of the spherical element 217 and the inner surface of the seat 213, thus ensuring effective locking of the joint.

As can be seen, the dimensions of the housing seat 213 are such that the surface of the spherical element 217 in contact with it is large and this promotes a secure and long-lasting locking of the joint 205 in the desired position.

Then, the elongated element 216 is engaged with the central body 204, thus obtaining a connection between the first member 202 and the central body 204 according to the desired angular directions.

If the ball joint 205 has to be disconnected from the respective first member 202, the same is done in reverse. The ball joint 205 is structurally simple and easy to apply. The present embodiment of a fixing device 200, similarly to the previous embodiments, has the advantage of being easy to adjust and apply to the location of the fracture to be treated.

To assemble the first member 202 and the second member 203 to the central body 204, through the first ball joint 205 and the second ball joint 206, it is sufficient to proceed as described above and then connect the elongated element 216 of the respective joints 205 and 206 to the central body 204.

The fixing device 200 according to the present invention has a first clamp 207, a second clamp 208 and a third clamp 209 for the connection to the fractured bone portion to be treated. The first clamp 207 and the second clamp 208 are mobile in an articulated manner with respect to the third clamp 209.

More specifically, the first clamp 207 is associated in a mobile manner with the first member 202, in the longitudinal direction.

In particular, the first clamp 207 comprises a base 225. There is also an attachment screw 227 for clamping the first clamp 207 against its base 225.

The attachment screw 227, therefore, allows the removable connection between an upper portion of the clamp 207 and its base 225 according to ways known in the field.

By acting on the attachment screw 227, it is possible to loosen the first clamp 207 from the respective base 225 and then rotate it about a vertical axis, corresponding to that of the screw 227, not shown in the figures. In this way it is possible to modify the orientation of the clamp 207 with respect to the longitudinal direction of the first member 202 and/or of a linear guide 226, formed in the first member 202, in the longitudinal direction, thus varying the position and orientation of the pins or of the attachment screws to be applied to the bone portion to be treated.

The first clamp 207, and/or specifically its base, is slidably associated along the linear guide 226.

The linear guide 226 comprises a seat 228, for example a slot or a through recess going through the first member 202, formed in the longitudinal direction along the first member 202, and means 229 for adjusting the position of the first clamp 207 along the first member 202.

The adjustment means 229 comprise an adjustment screw (not illustrated in the drawings), directed in the seat 228 in the longitudinal direction along the first member 202, which adjustment screw is associated, with a screw-and-nut type coupling, with the base 225 of the first clamp 207.

Therefore, by rotating the adjustment screws the first clamp 207 moves along the first member 202 in seat 228.

The second clamp 208 is associated in a mobile manner with the second member 203 in an analogous way to what has been described above relative to the connection of the first clamp 207 to the first member 202.

With such a configuration of the clamps 207 and 208, the surgeon can rotate the first clamp 207 and/or the second clamp 208 around respective vertical axes, modifying accordingly the orientation of the connection pins engageable therein and thus adapting the configuration of the fixing device 200 to the shape of the bone portion to be treated.

The third clamp 209, similarly to the first clamp 207 and to the second clamp 208, comprises an upper portion 238 and a lower portion 239.

Figure 11:
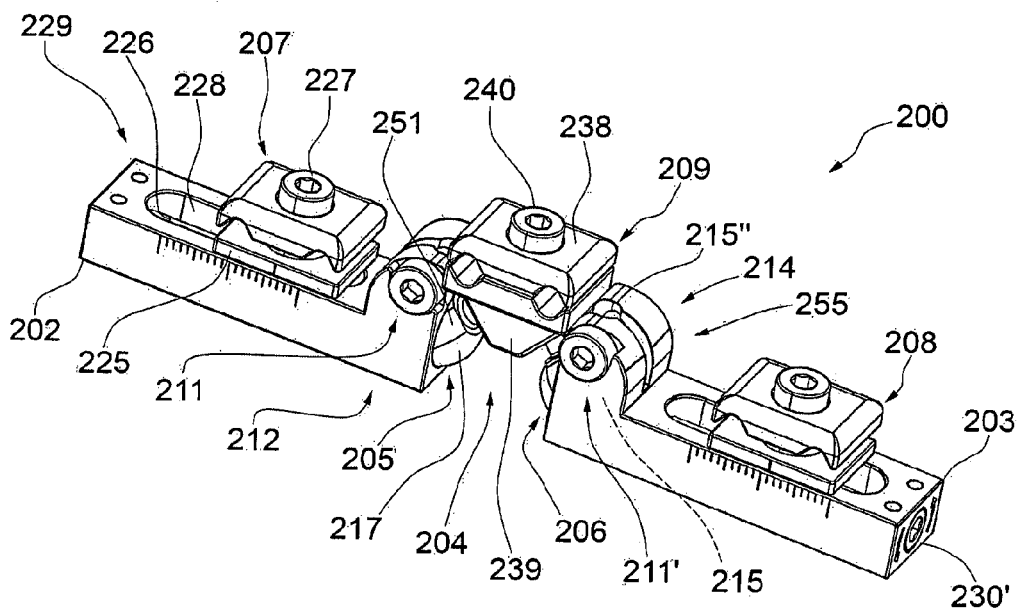
FIG. 11 is a perspective view of a further embodiment of the external fixing device according to the present invention.
Figure 12:
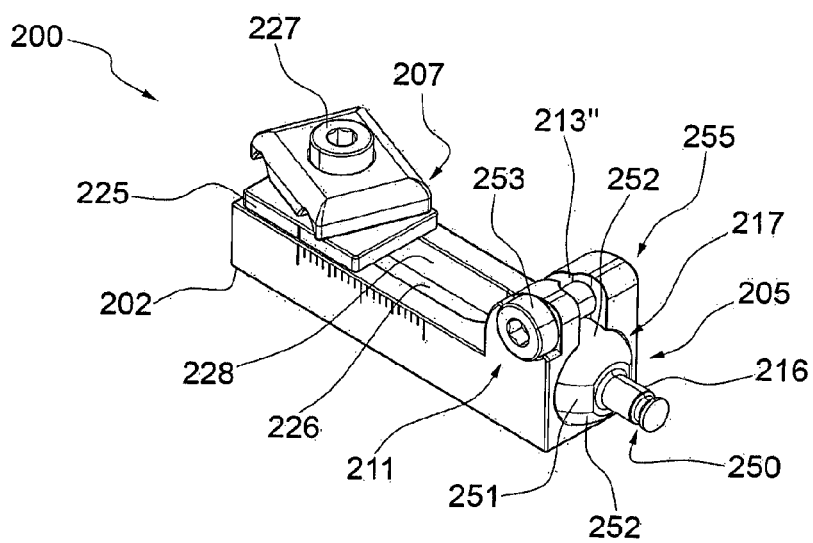
FIG. 12 is a perspective view of a detail of the external fixing device according to FIG. 11.

In the version illustrated in FIG. 11, the upper portion 238 is removably connected to the lower portion 239 through an attachment screw 240 and, similarly to what has been described above for the first clamp 207 and the second clamp 208, it is possible to vary the orientation of the third clamp 209 by rotating it about a vertical axis, corresponding to that of the screw 240, not shown in the figures.

The presence of a third clamp 209, at the central body 204, allows the effective use of the external fixing device 200 for the treatment of any type of heel bone fracture, both in the case of simple fractures and in the case of complex fractures.

The fixing device 200, according to the present invention, indeed, has a first clamp 207, a second clamp 208 and a third clamp 209 that can be articulated with respect to one another substantially into any reciprocal position in space.

In particular, the third clamp 209 acts as a reference element for the connection of the fixing device 200 to the location to be treated. As can be seen, in all of the embodiments of the external fixing device described above the first clamp 7, 107, 207 and the second clamp 8, 108, 208 are mobile in an articulated manner with respect to the third clamp 9, 109, 209.

In particular, the first clamp 7, 107, 207 and the second clamp 8, 108, 208 are mobile along at least three directions perpendicular to one another.

The possibility of directing the first clamp 7, 107, 207 and the second clamp 8, 108, 208 in space with respect to the third clamp 9, 109, 209 along a substantially unlimited number of directions gives the surgeon a great degree of freedom, during an operation, in the connection of the fixing device 1, 100, 200 itself to the bone portion to be treated, even in the presence of complex fractures.

This overcomes the limitations of external fixing devices of the prior art wherein the first and second member are available to one another along a single possible direction of space or, at most, in a single plane of space.

The invention thus conceived can undergo numerous modifications and variants all of which are covered by the inventive concept.

Moreover, all of the details can be replaced by other technically equivalent ones. In practice, the materials used, as well as the contingent shapes and sizes, can be of any suitable type, depending on the requirements, without for this reason departing from the scope of protection of the following claims.

The invention claimed is:

1. An external fixing device for the treatment of bone fractures comprising a first member, a second member, a central body arranged between said first member and said second member, a first ball joint for the articulated connection of said first member with said central body, a second ball joint for the articulated connection of said second member with said central body, locking means operatively associated with said first ball joint and said second ball joint, said locking means being designed to allow/prevent the articulation of said first member and second member respectively, with respect to said central body, wherein said first member comprises a first clamp, said second member comprises a second clamp and said central body comprises a third clamp, wherein said first clamp, second clamp and said third clamp are suitable for housing pins or screws, to ensure the connection of said fixing device to the bone portions to be treated, wherein said first clamp is associated in a moveable manner to said first member along a longitudinal direction (A, B), and said second clamp is associated in a moveable manner to said second member along a longitudinal direction (A', B'), wherein said external fixing device comprises means for adjusting the position of at least one of said first clamp along said first member and the position of said second clamp along said second element, and wherein said adjustment means comprise an adjustment screw longitudinally oriented along said first member and associated with a base portion of said first clamp by a screw-and-nut type coupling, and a further adjustment screw longitudinally oriented along said second member and associated with a base portion of said second clamp by a screw-and-nut type coupling, wherein the position of said first clamp along said first member and the position of said second clamp along said second member is adjusted by rotating a respective of said adjustment screws.

2. The external fixing device according to claim 1, wherein said external fixing device is an external fixing device for heel bone.

3. The external fixing device according to claim 1, wherein said first clamp is articulated to said third clamp, by means of said first ball joint, along at least three planes orthogonal with each other.

4. The external fixing device according to claim 1, wherein said second clamp is articulated to said third clamp, by means of said second ball joint, along at least three planes orthogonal with each other.

5. The external fixing device according to claim 1, wherein said first member comprises a seat for housing said first ball joint.

6. The external fixing device according to claim 5, wherein said second member comprises a seat for housing said second ball joint.

7. The external fixing device according to claim 6, wherein said first ball joint and said second ball joint each comprise an elongated element and a spherical element, said elongated element being coaxial to and extending outward from said spherical element.

8. The external fixing device according to claim 7, wherein said spherical element comprises a substantially cylindrical central portion arranged between two substantially cap-shaped portions.

9. The external fixing device according to claim 8, wherein a cross section of said substantially cylindrical central portion comprises a radius (r) lower than a radius of curvature (R) of each of said substantially cap-shaped portions, so that said spherical element has smaller overall dimensions in a plane parallel to said bases of said substantially cylindrical central portion.

10. The external fixing device according to claim 9, wherein each of said seat for housing the respective ball joint delimits a cap-shaped region having a radius of curvature slightly greater than said radius of curvature (R) of said substantially cap-shaped portions and has a substantially circular inlet mouth having a radius slightly larger than said radius (r) of said circular section of said substantially cylindrical central portion but smaller than the radius of curvature (R) of said substantially cap-shaped portions.

11. The external fixing device according to claim 10, comprising locking means for stopping the rotation of said spherical element in the respective seat.

12. The external fixing device according to claim 11, wherein said seats are provided with an upper opening for receiving, in use, said elongated element of said joint.

13. The external fixing device according to claim 12, wherein at said upper opening and at opposite sides therefrom, said member is provided with two plates of a jaw-type end designed to lock/fasten in position said spherical element of said joint in the respective seat.

14. The external fixing device according to claim 13, wherein said locking means comprise a screw engageable in corresponding threaded seats obtained in said plates of said jaw-type end of each member above said respective seat.

15. The external fixing device according to claim 11, wherein, once said spherical element is locked in position by said locking means, said surface of said substantially cap-shaped portions is uniformly in abutment on said internal surface of said seat, thereby guaranteeing a wide engagement surface between said spherical element and said seat.

16. The external fixing device according to claim 7, wherein the portion of said elongated element extending outward from said spherical element is threaded.

17. The external fixing device according to claim 16, wherein said threaded is engageable in a corresponding threaded seat obtained in said central body.

18. The external fixing device according to claim 16, wherein said elongated element comprises at one end thereof arranged inside said spherical element an enlarged portion designed to cause a radial expansion of said spherical element.

19. The external fixing device according to claim 16, wherein said spherical element is provided with at least one radial notch designed to allow the radial expansion of said spherical element.

20. The external fixing device according to claim 16, wherein said locking means comprise at least one adjustment nut operatively associated to said ball joint along respective threaded portions of said elongated elements.

21. The external fixing device according to claim 16, wherein said elongated element comprises at least one guide element, configured as a tab, pin or the like, wherein said guide element extends from said elongated element and is slideable along said at least one radial notch of said spherical element.

22. The external fixing device according to claim 16, comprising a shim element housable into said seat, arranged between said first member and said first ball joint, designed to vary the distance of said first member from said central body and/or comprising a shim element housable in said seat, arranged between said second member and said second ball joint, designed to vary the distance of said second member from said central body.

23. The external fixing device according to claim 1, wherein said locking means are removably connected to an end of a respective member by means of a screw, designed to bring into abutment said locking means against a respective ball joint.

\* \* \* \* \*